(12) United States Patent
White et al.

(10) Patent No.: US 11,359,751 B2
(45) Date of Patent: Jun. 14, 2022

(54) TAMPER-EVIDENT COVER

(71) Applicant: Bio Pure Technology Limited, Waterlooville (GB)

(72) Inventors: Nick White, Falmouth Cornwall (GB); Chris Sillitoe, Cornwall (GB)

(73) Assignee: Bio Pure Technology Limited, Waterlooville (GB)

( * ) Notice: Subject to any disclaimer, the term of this patent is extended or adjusted under 35 U.S.C. 154(b) by 817 days.

(21) Appl. No.: 16/093,807

(22) PCT Filed: Apr. 20, 2017

(86) PCT No.: PCT/GB2017/051106
§ 371 (c)(1),
(2) Date: Oct. 15, 2018

(87) PCT Pub. No.: WO2017/182814
PCT Pub. Date: Oct. 26, 2017

(65) Prior Publication Data
US 2020/0080675 A1 Mar. 12, 2020

(30) Foreign Application Priority Data

Apr. 21, 2016 (GB) .................................... 1606951
Nov. 25, 2016 (GB) .................................... 1620014

(51) Int. Cl.
*F16L 37/084* (2006.01)
*A61M 39/10* (2006.01)
(Continued)

(52) U.S. Cl.
CPC ........ *F16L 37/084* (2013.01); *A61M 39/1011* (2013.01); *F16B 2/18* (2013.01);
(Continued)

(58) Field of Classification Search
CPC ......... F16L 37/084; F16L 3/1025; F16B 2/18; F16B 7/0426
See application file for complete search history.

(56) References Cited

U.S. PATENT DOCUMENTS

| 4,151,745 A | 5/1979 | Cordy et al. |
| 5,018,768 A | 5/1991 | Palatchy |

(Continued)

FOREIGN PATENT DOCUMENTS

| CN | 102131468 A | 7/2011 |
| CN | 102705317 A | 10/2012 |

(Continued)

OTHER PUBLICATIONS

Notice of Reasons for Rejection, Japanese Patent Application No. 2020-112914, dated Apr. 20, 2021.
(Continued)

*Primary Examiner* — Matthew Troutman
*Assistant Examiner* — James A Linford
(74) *Attorney, Agent, or Firm* — Hontgman LLP

(57) ABSTRACT

A tamper-evident cover for a component, the component comprising: first and second portions; and an actuator mechanism for moving the first and second portions or allowing the first and second portions to move relative to one another; wherein the cover comprises: a cover portion defining a cavity configured to receive the actuator mechanism of the component so as to prevent access to the actuator mechanism from the exterior of the cover portion; and a retention barb connected to the cover portion and housed within the cavity formed by the cover portion such that it is inaccessible from the exterior of the cover portion, the retention barb being configured to engage with the component so as to retain the cover portion over the actuator mechanism.

2 Claims, 18 Drawing Sheets

(51) Int. Cl.
*F16B 2/18* (2006.01)
*F16B 7/04* (2006.01)
*F16L 3/10* (2006.01)

(52) U.S. Cl.
CPC .......... *F16B 7/0426* (2013.01); *F16L 3/1025* (2013.01); *F16L 3/1075* (2013.01); *F16L 2201/10* (2013.01); *F16L 2201/44* (2013.01)

(56) References Cited

U.S. PATENT DOCUMENTS

| | | | |
|---|---|---|---|
| 5,305,978 | A | 4/1994 | Current |
| 5,385,373 | A * | 1/1995 | Love ................... F16B 41/007 24/16 PB |
| 2004/0094958 | A1 | 5/2004 | Treverton et al. |
| 2009/0119886 | A1 | 5/2009 | Werth |
| 2009/0208277 | A1 | 8/2009 | Werth |
| 2010/0242552 | A1 | 9/2010 | Sayegh et al. |
| 2012/0227221 | A1 | 9/2012 | Whitaker et al. |
| 2014/0151514 | A1 * | 6/2014 | Asai ........................ H02G 3/34 248/74.1 |
| 2016/0053926 | A1 | 2/2016 | Whitaker |

FOREIGN PATENT DOCUMENTS

| | | |
|---|---|---|
| CN | 202561267 U | 11/2012 |
| CN | 104534178 A | 4/2015 |
| CN | 204403575 U | 6/2015 |
| DE | 2552100 A1 | 6/1977 |
| EP | 1693609 A2 | 8/2006 |
| EP | 2666513 A1 | 11/2013 |
| GB | 890353 A | 2/1962 |
| GB | 2486538 A | 6/2012 |
| JP | S57-005964 A | 1/1982 |
| JP | 2006-046537 A | 2/2006 |
| JP | 2009-503410 A | 1/2009 |
| JP | 2012-525556 A | 10/2012 |
| KR | 10-0725774 | 5/2007 |
| WO | 2010071812 A1 | 6/2010 |

OTHER PUBLICATIONS

Japanese Office Action for Japanese Application No. 2018-554560 dated Nov. 5, 2019 along with English translation.
U.K. Examination Report for Application GB1606951.0 dated Mar. 2, 2021.
U.K. Examination Report for Application GB1620014.9 dated Mar. 2, 2021.
First Chinese Office Action, Application No. CN 202010170325.X, dated Mar. 26, 2021.
Japanese Office Action, Japanese Patent Application No. 2020-112925, dated Mar. 23, 2021.
Preliminary Rejection issued by Korean Intellectual Property Office dated Feb. 12, 2020, relating to Application No. 10-2018-7028789 (machine translation of Office Action and Korean reference attched).
UK Search Report for Application GB1606951.0 dated Oct. 19, 2016,.
UK Search Report for Application GB1620014.9 dated May 18, 2017.
International Search Report for Application PCT/GB2017/051106 dated Nov. 21, 2017.
UK Exam Report, Application No. 19 215 906.9, dated Sep. 29, 2021.
Second Chinese Office Action, Application No. 202010170325.X, dated Sep. 28, 2021.
Brazil Office Action, Application No. BR112018070984-0, dated Sep. 28, 2021.
Japan Decision of Rejection, Application No. JP2020-112925, dated Oct. 19, 2021.

* cited by examiner

TAMPER-EVIDENT COVER

TECHNICAL FIELD

The invention relates to a tamper-evident cover, particularly but not exclusively for a clamp used to connect flanged tubes or connectors for use in the bio-technology, pharmaceutical and food industries.

BACKGROUND

The ability to quickly and effectively make fluid-tight connections between sanitary fittings is particularly important in the bio-technology, pharmaceutical and food industries where the fluid being conveyed must be isolated from the external environment in order to retain the sterile conditions.

For example, a tri-clamp fitting may be employed to connect a pair of hose tail fittings which are each inserted in a hose. A tri-clamp fitting generally comprises two semi-circular portions which are hingedly connected to one another. The free end of one of the semi-circular portions comprises a wingnut located on a bolt which can pivot relative to the semi-circular portion. The other semi-circular portion comprises a bifurcated portion which defines a slot that receives the bolt. The wingnut can be drawn into engagement with the bifurcated portion so as to lock the clamp in a closed position. The semi-circular portions comprise an inwardly facing tapered groove for drawing flanges of the hose tail fittings into sealing engagement, typically with a gasket therebetween.

SUMMARY

In accordance with an aspect of the invention there is provided a tamper-evident cover for a component, the component comprising: first and second portions; and an actuator mechanism for moving the first and second portions or allowing the first and second portions to move relative to one another; wherein the cover comprises: a cover portion defining a cavity configured to receive the actuator mechanism of the component so as to prevent access to the actuator mechanism from the exterior of the cover portion; and a retention barb connected to the cover portion and housed within the cavity formed by the cover portion such that it is inaccessible from the exterior of the cover portion, the retention barb being configured to engage with the component so as to retain the cover portion over the actuator mechanism.

The component may be a clamp, wherein the first and second portions are arcuate portions which are hingedly connected to one another and the actuator mechanism is a ratchet mechanism for locking the first and second arcuate portions in a closed position, the ratchet mechanism comprising a toothed rack provided with the second arcuate portion and a pawl provided with the first arcuate portion for engaging with the rack. The cavity of the cover portion may be configured to receive the ratchet mechanism of the clamp so as to prevent access to the pawl from the exterior of the cover portion.

The pawl of the clamp may comprise a release tab and a tab stop, and wherein the retention barb is configured to pass between the release tab and the tab stop and engage with the tab stop.

The cover portion may be formed by a first element and the retention barb formed by a second element, wherein the first and second elements are separable from one another such that the cover portion can be removed to provide access to the actuator mechanism.

The first and second elements may be connected by a pull-tab which is removable to separate the first and second elements.

In accordance with another aspect of the invention there is provided a clamp comprising: a first arcuate portion; a second arcuate portion hingedly connected to the first arcuate portion; and a ratchet mechanism for locking the first and second arcuate portions in a closed position; wherein the ratchet mechanism comprises a linear rack provided with the second arcuate portion and a pawl provided with the first arcuate portion for receiving the linear rack; wherein the linear rack comprises one or more asymmetrical teeth; wherein the pawl comprises a plurality of fingers which are biased into engagement with the teeth of the linear rack.

The linear rack may comprise a plurality of toothed paths each comprising one or more asymmetrical teeth; wherein each of the plurality of fingers are configured to engage with the teeth of one of the plurality of toothed paths.

The teeth of a first path of the plurality of toothed paths may differ from the teeth of a second path.

The dimensions of the teeth of the first path may differ from the teeth of second path.

The first path may comprise one or more teeth having a larger height than the teeth of the second path, wherein the teeth of the first path are positioned so as to provide tactile/audible feedback to a user to indicate an optimum clamping force.

First and second fingers of the plurality of fingers which engage the first and second paths respectively may be biased with different biasing forces.

The teeth of the first path may be offset from the teeth of the second path and/or first and second fingers which engage the first and second paths respectively may be offset from one another so that the first and second fingers engage alternately with the first and second toothed paths.

The plurality of toothed paths may comprise first and second paths which are provided on opposing surfaces of the linear rack.

The first and second paths may be provided on opposing lateral surfaces of the linear rack.

The position of at least one of the plurality of fingers can be changed to engage with a different one of the plurality of toothed paths.

The pawl may be formed by a module which is detachably connected to the first arcuate portion.

The module may be selected from a plurality of interchangeable modules.

The positions of the first and second fingers may differ for each of the plurality of interchangeable modules.

The plurality of fingers may be provided on a plurality of actuation buttons which are independently actuable.

The clamp may be formed from a reinforced polymeric materials.

In accordance with another aspect of the invention, there is provided a clamp comprising: a first arcuate portion; a second arcuate portion hingedly connected to the first arcuate portion; and a ratchet mechanism for locking the first and second arcuate portions in a closed position; wherein the ratchet mechanism comprises a linear rack provided with the second arcuate portion and a pawl provided with the first arcuate portion for receiving the linear rack; wherein the linear rack comprises one or more asymmetrical teeth and the pawl comprises a finger which is configured to engage with the teeth of the linear rack; wherein the pawl is formed by a module which is detachably connected to the first arcuate portion.

In accordance with another aspect of the invention, there is provided a clamp comprising: a first arcuate portion comprising a hinge arm which defines a recess; a second arcuate portion comprising a shaft which is received by the recess in a snap-fit so as to hingedly connect the first and second arcuate portions; wherein the clamp has an open position and a closed position and wherein the first and second arcuate portions are assembled in an assembly position; wherein the first or second arcuate portion comprises a cam surface which contacts an opposing surface of the other of the first and second arcuate portions during a transition between the assembly position and the open position so as to force the shaft towards the hinge arm.

BRIEF DESCRIPTION OF THE DRAWINGS

For a better understanding of the invention, and to show more clearly how it may be carried into effect, reference will now be made, by way of example, to the accompanying drawings, in which:—

DETAILED DESCRIPTION

Figure 1:
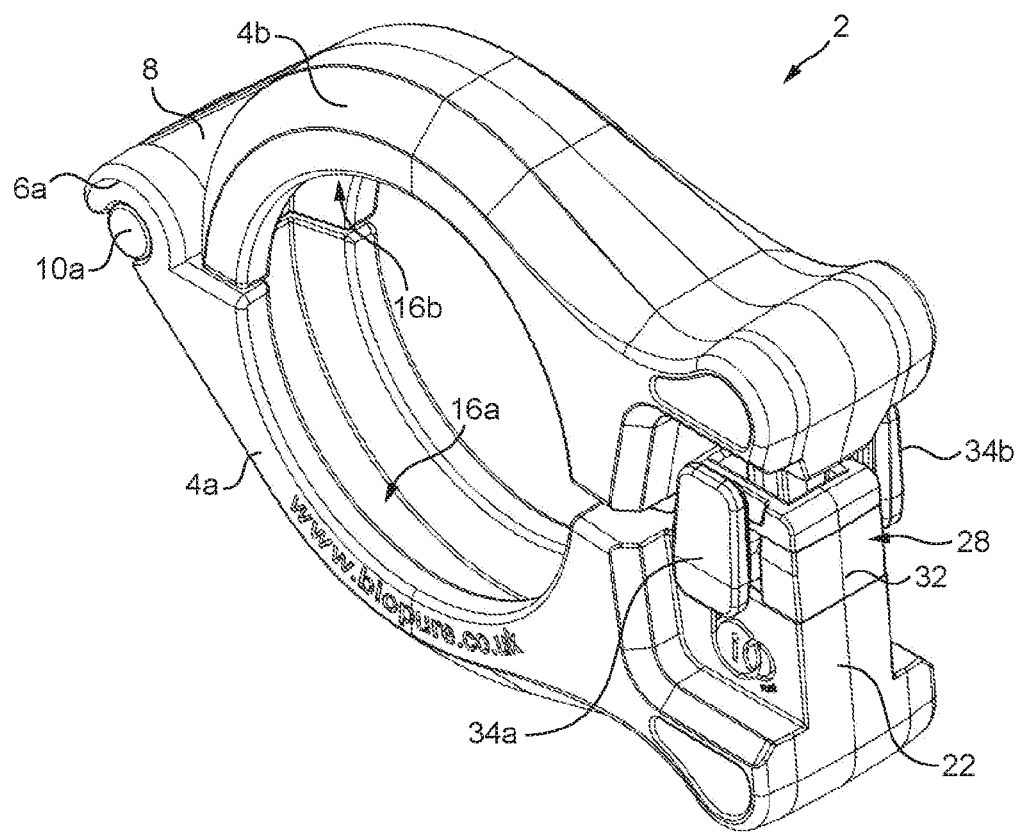
FIG. 1 is a perspective view of a clamp according to an embodiment of the invention in a closed position.
Figure 2:
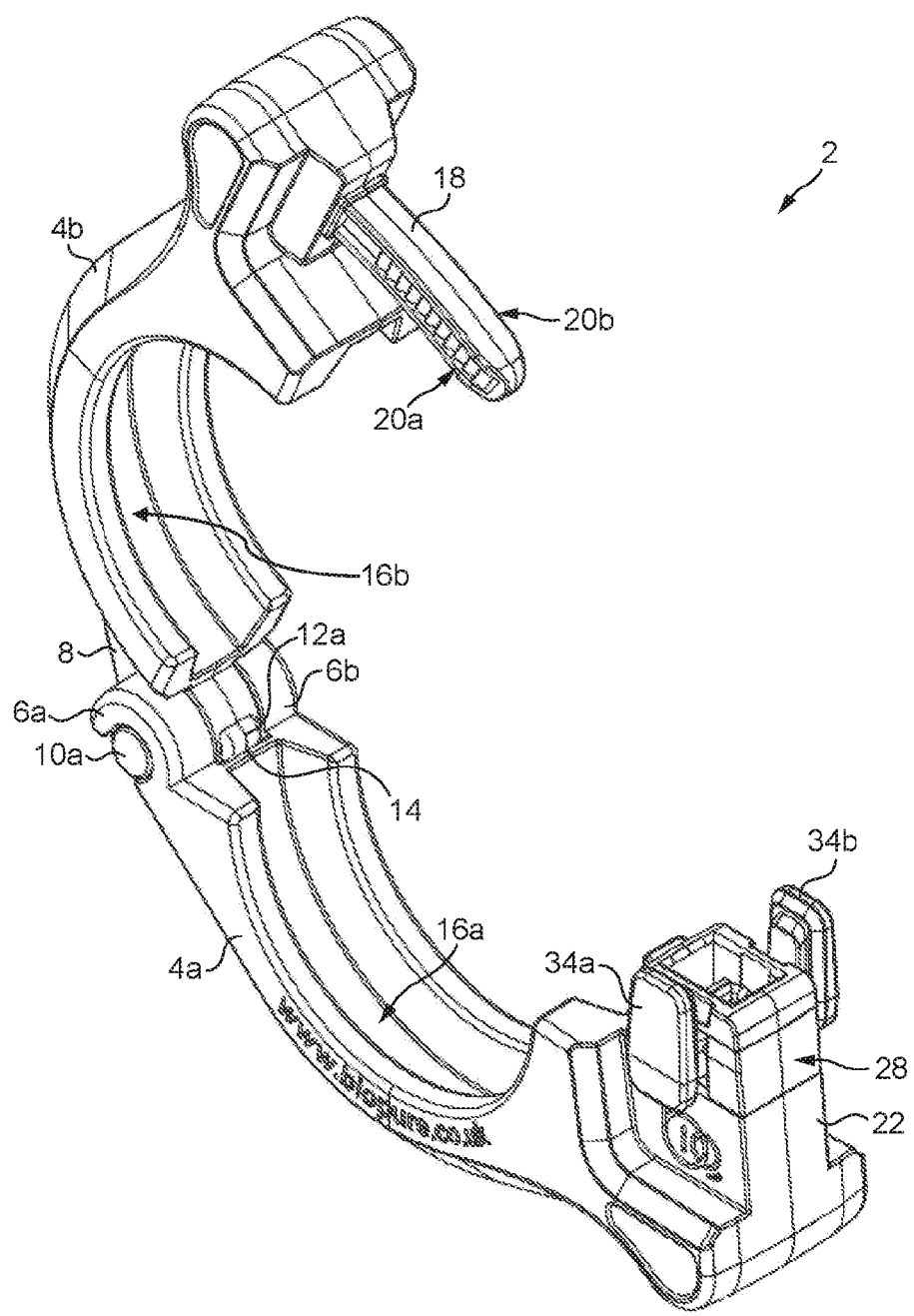
FIG. 2 is a perspective view of the clamp in an open position.

FIGS. 1 and 2 show a clamp 2 according to an embodiment of the invention. The clamp 2 comprises a first, lower arcuate portion 4a and a second, upper arcuate portion 4b.

The first and second arcuate portions 4a, 4b are hingedly connected to one another. Specifically, the first arcuate portion 4a comprises a pair of hinge arms 6a, 6b which are spaced laterally from one another. The hinge arms 6a, 6b are arcuate and have extent which is slightly greater than 180°. The hinge arms 6a, 6b thus define a recess.

The second arcuate portion 4b is provided with a hinge lobe 8. A cylindrical stub shaft 10a, 10b projects from each lateral side of the hinge lobe 8. The stub shafts 10a, 10b are sized to be received within the recess defined by the hinge arms 6a, 6b to form a snap-fit connection. The first and second arcuate portions 4a, 4b are thus able to rotate between a closed position, as shown in FIG. 1, and an open position, as shown in FIG. 2.

Figure 3:
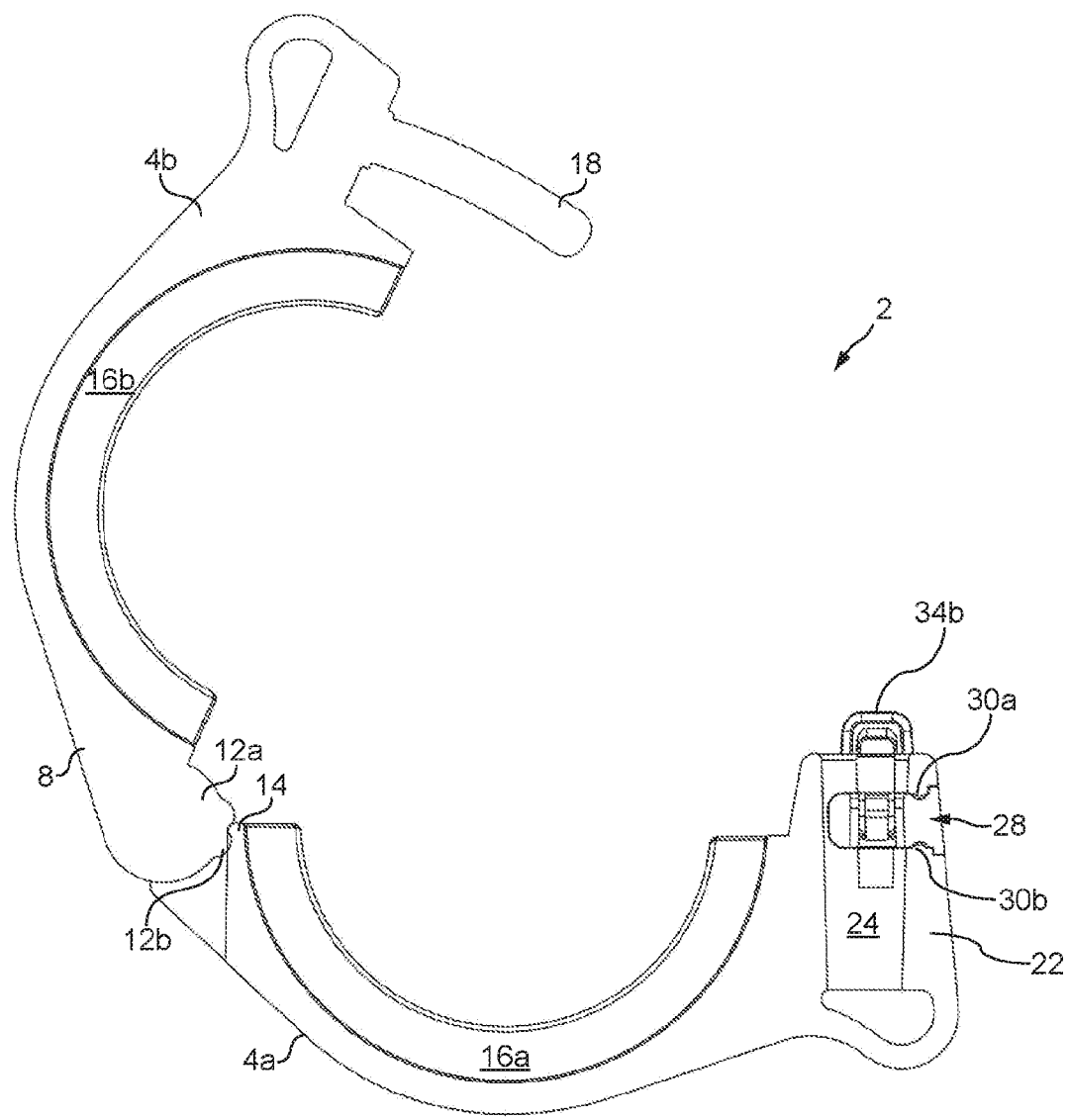
FIG. 3 is a cross-sectional view of the clamp in the open position.
Figure 4:
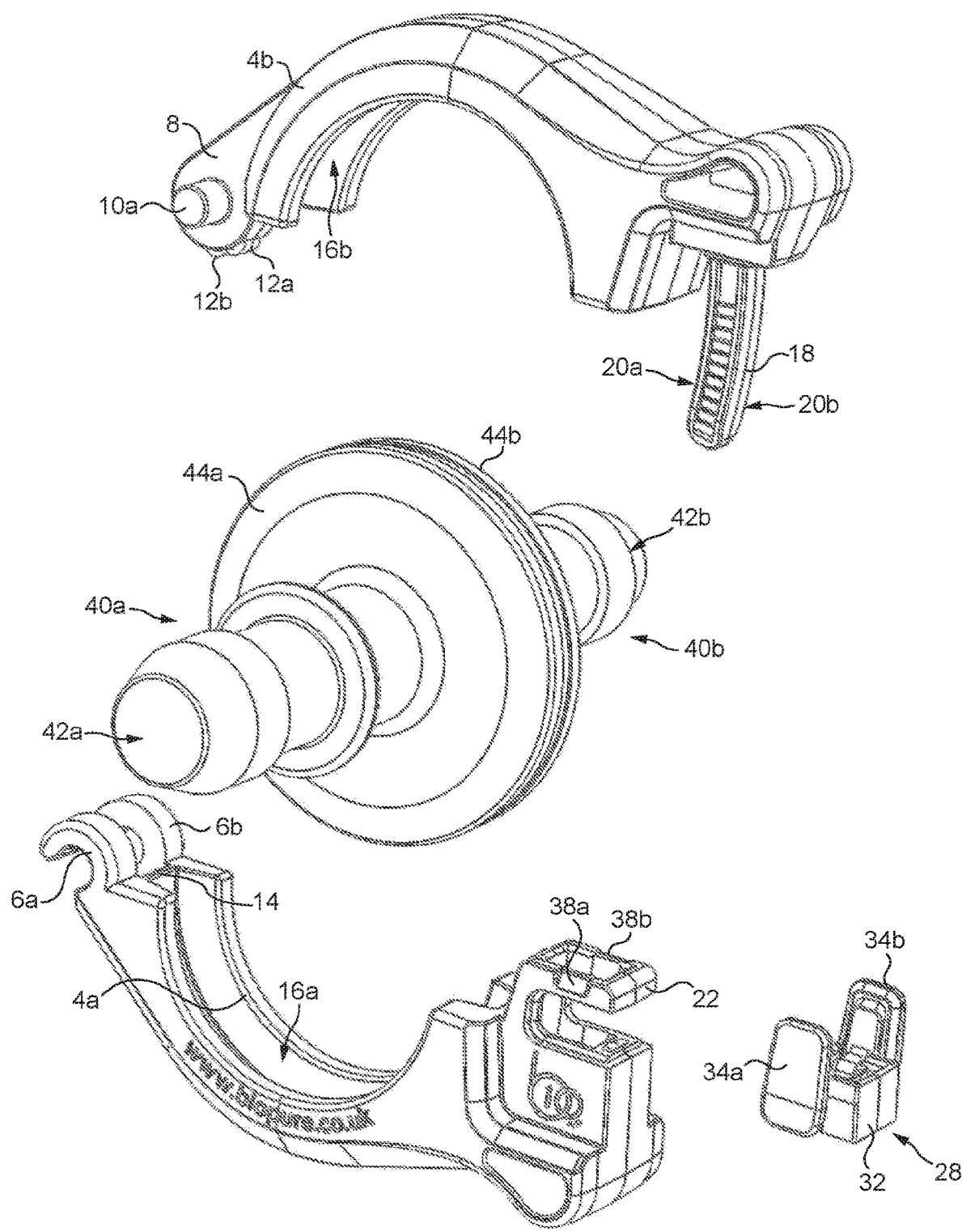
FIG. 4 is an exploded view of the clamp.

As shown particularly in FIGS. 3 and 4, a radial, end surface of the hinge lobe 8 is provided with a pair of detent protrusions 12a, 12b which are angularly spaced from one another about the hinge lobe 8. The detent protrusions 12a, 12b interface with an edge 14 of the first arcuate portion 4a. Specifically, when opening the clamp 2, the detent protrusion 12a must be forced over the edge 14, such that the detent protrusions 12a, 12b straddle the edge 14, as is best shown in FIG. 3. In this position, the detent protrusion 12a prevents the clamp 2 from closing and the detent protrusion 12b prevents the clamp 2 from opening further. Thus, the detent protrusions 12a, 12b retain the clamp in the open position to improve ease of use. The clamp 2 may, however, be opened further in order to release the stub shafts 10a, 10b from the hinge arms 6a, 6b in order to detach the second arcuate portion 4b from the first arcuate portion 4a by applying sufficient force to force the detent protrusion 12b over the edge 14. Similarly, the clamp can be closed by applying sufficient force to force the detent protrusion 12a over the edge 14. The detent protrusions 12a, 12b may be allowed to pass over the edge 14 through deformation of the clamp 2. For example, deformation may occur in one or more of: the detent protrusions 12a, 12b, edge 14, the stub shafts 10a, 10b and the hinge arms 6a, 6b. The detent protrusions 12a, 12b may be movable and biased outwardly by a biasing mechanism, such as a spring or the like, such that deformation of the detent protrusions 12a, 12b is permitted by deformation of the biasing mechanism.

As described previously, the first and second arcuate portions 4a, 4b are hingedly connected to one another by a snap-fit connection. The snap-fit connection is formed with the first and second arcuate portions 4a, 4b opened at an angle which exceeds that shown in FIG. 2 such that both of the detent protrusions 12a, 12b are received on an interior side of the edge 14. In this position, the opening of the recess formed by the hinge arms 6a, 6b may sufficiently large to receive the stub shafts 10a, 10b with relatively little or no resistance. In this position, there is therefore significant laxity or slack in the hinged joint. However, when the clamp 2 is moved to the normally open position, with the detent protrusions 12a, 12b straddling the edge 14, the stub shafts 10a, 10b are held securely by the hinge arms 6a, 6b and this level of interference is maintained between the open and closed positions. Therefore, over the functional range of movement of the clamp 2, the hinged connection exhibits a very low amount of play. The transition of the hinged connection from a loose connection which enables easy assembly to a tight connection which improves user experience (exuding quality) may be achieved by providing a cam profile on one or more of the interface surfaces between the first and second arcuate portions 4a, 4b, such as one or more of the hinge surfaces formed by the hinge arms 6a, 6b and the stub shafts 10a, 10b and/or the end surface of the hinge lobe 8 and an opposing surface of the first arcuate portion 4a.

The loose connection during assembly may reduce the likelihood of spallation/particulate being removed during assembly, which is particularly important in a clean-room environment. Having a wide opening which easily receives the stub shafts 10a, 10b is also particularly useful where the clamp 2 is constructed from a stiff material, such as a reinforced polymeric material like glass-reinforced nylon.

The first and second arcuate portions 4a, 4b each comprise a semi-circular groove 16a, 16b. Side walls of the grooves 16a, 16b are angled with respect to one another such that the width of the groove tapers in a radial direction (i.e. the groove is narrower at a larger radius than at a smaller radius). In the closed position shown in FIG. 2, the semi-circular grooves 16a, 16b of the first and second arcuate portions 4a, 4b meet to form a substantially continuous circular channel.

The distal, free ends of the first and second arcuate portions 4a, 4b are provided with a ratchet mechanism for locking the clamp 2 in the closed position. Specifically, the second arcuate portion 4b is provided with a tongue 18 (rack) which projects from the second arcuate portion 4b in a substantially circumferential direction. The tongue 18 comprises opposing lateral surfaces 20a, 20b which are each provided with one or more teeth.

The first arcuate portion 4a is provided with a receiving portion 22. The receiving portion 22 defines a cavity 24 (see FIG. 3, particularly) which receives the tongue 18. The receiving portion 22 defines a slot 26 (see FIG. 4, particularly) which opens outwardly and receives a separate pawl element 28. The pawl element 28 is detachably connected to the receiving portion 22 via a snap-fit connection. In particular, as shown in FIG. 3, the receiving portion 22 comprises an upper ridge 30a and a lower ridge 30b which project into the slot 26. The pawl element 28 comprises complementary upper and lower grooves (not specifically labelled) formed in a body portion 32 of the pawl element 28 which receive the upper and lower ridges 30a, 30b to retain the pawl element 28 within the slot 26. The snap-fit connection between the pawl element 28 and the receiving portion 22 is not required to withstand in-use loads which are substantially perpendicular to the orientation of the snap-fit connection.

The pawl element 28 comprises a pair of actuation buttons 34a, 34b which are disposed at opposing lateral sides of the clamp 2.

Figure 5:
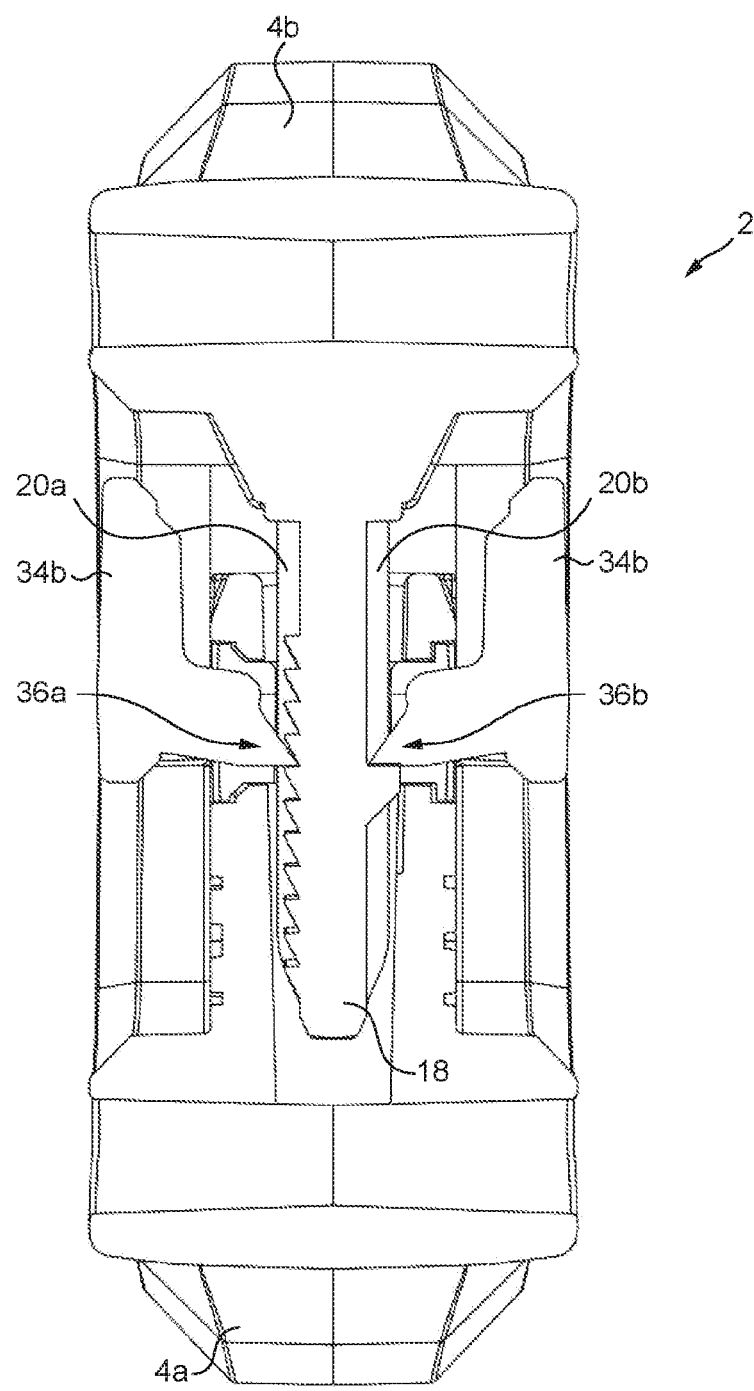
FIG. 5 is a cross-sectional view showing a ratchet mechanism of the clamp.
Figure 6:
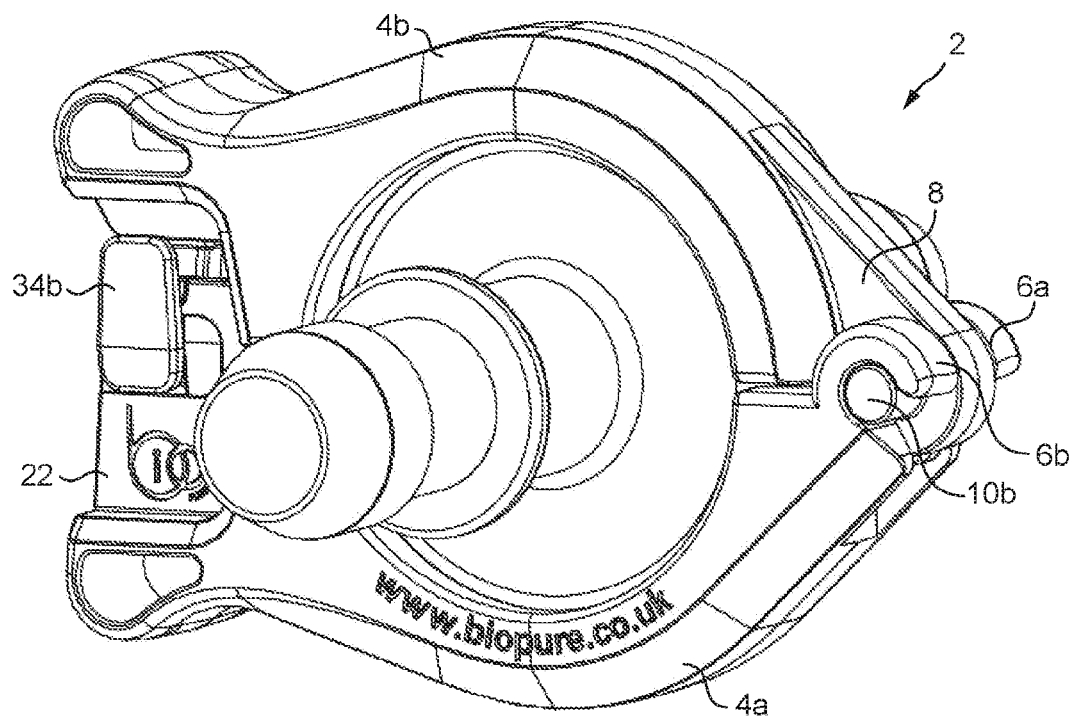
FIG. 6 is a perspective view of the clamp in use.

As best shown in FIG. 5, each of the actuation buttons 34a, 34b is provided with a finger 36a, 36b toward its lower end. The fingers 36a, 36b of the actuation buttons 34a, 34b are configured to engage with the teeth of the opposing lateral surfaces 20a, 20b of the tongue 18 respectively.

Each of the actuation buttons 34a, 34b is connected to the body portion 32 of the pawl element 28 by a torsion bar. The torsion bars bias the actuation buttons 34a, 34b so that the fingers 36a, 36b are biased towards one another and into engagement with the teeth of the opposing lateral surfaces 20a, 20b of the tongue 18. The fingers 36a, 36b may be drawn away from the tongue 18 by squeezing the upper ends of the actuation buttons 34a, 34b toward one another such that the actuation buttons 34a, 34b rotate about the torsion bars. This action generates a torque in the torsion bar which forces the fingers 36a, 36b back towards one another once the actuation buttons 34a, 34b are released. As shown in FIG. 4, the receiving portion 22 is provided with a pair of angled recesses 38a, 38b which allow the actuation buttons 34a, 34b to be rotated as they are depressed.

The tongue 18 is curved along its length so that the teeth are kept parallel to the pawl element 28 during rotation of the second arcuate portion 4b about the hinge.

Figure 7:
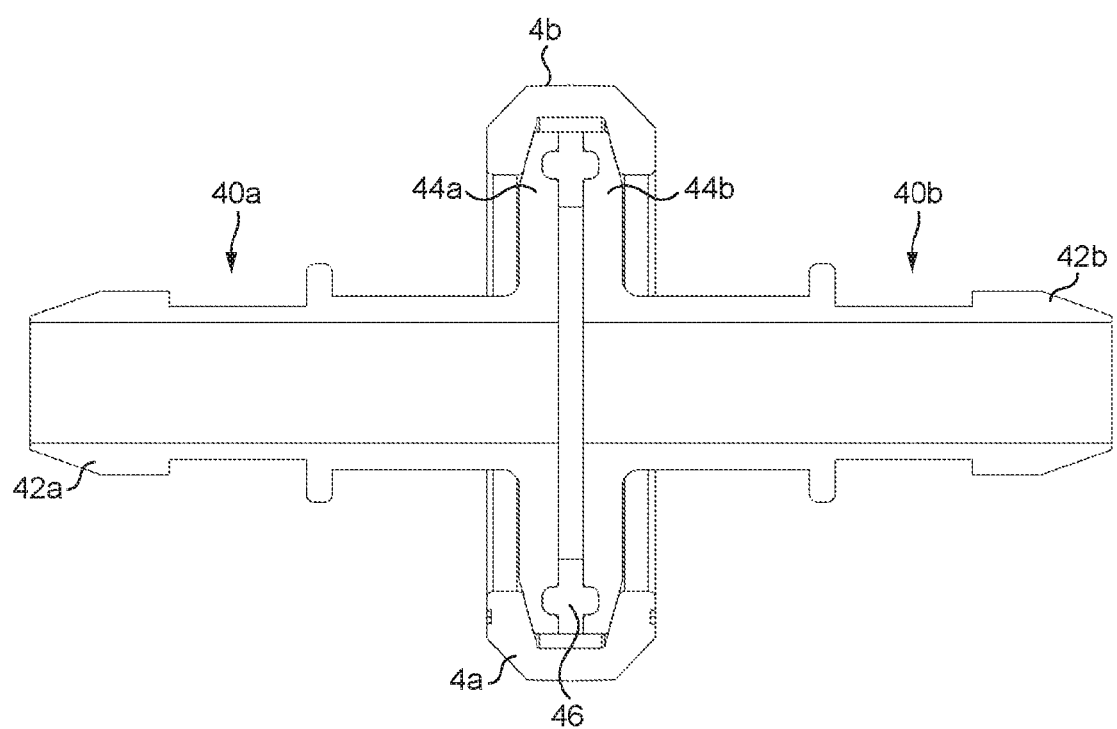
FIG. 7 is a cross-sectional view of the clamp in use.

As shown particularly in FIG. 7, the clamp 2 may be employed to connect a pair of hose tail fittings 40a, 40b used to join two sections of hose (not shown) together. The tail fittings 40a, 40b comprise a barb 42a, 42b which is inserted into the hose and a flange 44a, 44b.

In use, with the clamp 2 in the open position shown in FIG. 2, the flanges 44a, 44b are received in the semi-circular groove 16a of the first arcuate portion 4a with a gasket seal 46 disposed therebetween. As shown, the opposing surfaces of the flanges 44a, 44b may be provided with circular grooves for receiving the gasket seal 46. The clamp 2 is then closed such that the second arcuate portion 4b is received over the flanges 44a, 44b. In this closed position, the tongue 18 is received in the receiving portion 22 and the teeth of the tongue 18 engage with the fingers 36a, 36b of the pawl element 28.

The teeth of the tongue 18 are asymmetrical such that the fingers 36a, 36b ride over the teeth as the tongue 18 is inserted into the receiving portion 22, but engage with the teeth if the tongue 18 is retracted from the receiving portion 22. The first and second arcuate portions 4a, 4b can therefore be squeezed together such that the teeth progressively pass the fingers 36a, 36b. Owing to the tapered geometry of the grooves 16a, 16b, this action causes the flanges 44a, 44b to be forced toward one another, compressing the gasket seal 46 disposed therebetween. The clamp 2 is therefore able to provide a fluid-tight seal between the tail fittings 40a, 40b and the ratchet mechanism ensures that the first and second arcuate members 4a, 4b are retained in the closed position at the desired level of compression.

In order to release the tail fittings 40a, 40b from the clamp 2, the actuation buttons 34a, 34b are depressed, as described previously, so that the fingers 36a, 36b no longer engage with the teeth thereby allowing the tongue 18 to be freely removed from the pawl element 28 and the receiving portion 22.

As described previously, the tongue is provided with teeth of both of the opposing lateral surfaces 20a, 20b. This provides a number of benefits and options for the clamp 2.

In particular, the teeth may differ from one side to the other in their number, position, spacing (i.e. frequency/pitch), dimensions (e.g. height), etc. For example, as shown in FIG. 5, the lateral surface 20a may comprise a plurality of teeth having a fine pitch (akin to that of a cable-tie) and the opposing lateral surface 20b may comprise only a single tooth which is larger in height than the teeth of the lateral surface 20a. The single, larger tooth of the surface 20b may be positioned partway along the tongue 18 at a position which corresponds to an optimum clamping force. Therefore, in operation, this would give the user an initial experience similar to tightening a cable-tie followed by a loud, positive snap when the clamp is in the intended position. The fingers 36a, 36b of the pawl element 28 may also differ from one another in their geometry and/or biasing to enable and/or accentuate this functionality.

The tongue 18 may also contain a plurality of separate paths on one or both of the surfaces 20a, 20b which are offset from one another across the width of the surface 20a, 20b. For example, the surface 20b may contain a plurality of paths each comprising a single tooth for signifying that the clamp 2 has been adequately tightened, but located at different positions to correspond to the proper position for different uses. For example, the different paths may correspond to the requirements for different industries or may correspond to different tail fittings and/or gasket seals. The clamp 2 may be configured to use the required tooth path by selecting from a plurality of interchangeable pawl elements 28 which have fingers provided in the correct location to track along the required path. Alternatively, a single pawl element 28 may be used which can be modified to move the finger(s) into the correct position for the required path.

A single, common design of the main clamp parts (i.e. the first and second arcuate portions 4a, 4b) can therefore cater for the many permutations of functionality offered by the configuration of the pawl element 28 (engineered to suit specific customer requirements).

In other embodiments, the teeth on the opposing lateral surfaces 20a, 20b may, however, be identical. Such an arrangement is beneficial in that the both of the actuation buttons 34a, 34b must be depressed in order to open the clamp 2. This redundancy avoids the clamp 2 being inadvertently released during service (including transportation and sterilization of complete fluid-path assemblies in bags). The teeth on each of the opposing lateral surfaces 20a, 20b may also differ along the length of the surface 20a, 20b. Such an arrangement may be used to provide the tactile, audible feedback described previously at certain positions.

The opposing lateral surfaces 20a, 20b may also use identical tooth profiles, but which are offset from one another. This effectively allows the combined pitch/resolution of the surfaces 20a, 20b to be doubled, as the fingers 36a, 36b alternately engage with the teeth. Consequently, a larger, more robust tooth profile can be used and still achieve the same pitch/resolution as a single-sided rack. Alternatively, the fingers 36a, 36b may be offset from one another to achieve the same effect. This could also be achieved using a single actuation button carrying a pair of offset fingers which engage a single toothed rack.

This may be particularly beneficial when using certain materials, such as glass-reinforced nylon. In particular, such materials may limit the effective engagement area of the teeth and therefore ultimately impose a minimum pitch of the teeth since the tooth profile should avoid sharp edges and therefore incorporate a slightly rounded edge. Moreover, a larger, more robust tooth profile is less likely to abrade and generate particulate contamination during normal operation.

Retaining the ability to fine-tune the gasket sealing pressure allows a user to change (particularly, tighten) the pressure slightly after sterilization (especially following autoclaving).

The ratchet mechanism is both Gamma stable and autoclave stable such that its performance is not compromised by any material degradation due to repeated cycles of cleaning and subsequent sterilization by autoclaving or gamma irradiation. The tongue 18 is resistant to creep/relaxation in use (especially during autoclaving in the assembled position) by virtue of the glass fiber reinforcement in the material.

The use of interchangeable pawl elements 28 which are detachably connected to the clamp allows the clamp to be tailored to specific applications and users. For example, in certain applications, the actuation buttons 34a, 34b may be removed or concealed such that the clamp can only be released by cutting, breaking or otherwise opening part of the pawl element. The clamp may require a specific tool for this purpose to prevent unauthorized release of the clamp. The pawl elements 28 may also be different colors to reflect a customer color scheme or to allow differentiation between clamps performing different functions. The pawl elements 28 can also be branded for specific customers and can include technical information, such as the date of manufacture.

Although not shown, the clamp may also provide visual as well as audible/tactile feedback regarding the position of the ratchet mechanism. For example, a simple scale of numbers may be used that are revealed to correspond with the position of the clamp.

The linear rack has been described as having teeth located on a lateral surface of the clamp. However, it will be appreciated that the teeth could be perpendicular to this and located on radial surfaces of the clamp. The teeth may also be provided only on one surface, rather than opposing surfaces. With this arrangement, a single set of teeth may be engaged by two fingers carried by a single actuation button to improve resolution or two separate actuation buttons (with the fingers offset laterally or along the length of the rack) to provide redundancy, as described previously. The rack may also comprise a plurality of toothed paths which are offset from one another (along the same surface, rather than on opposing surfaces, as described previously) and engaged by separate fingers carried by a single actuation button or multiple actuation buttons in order to provide the tactile feedback mechanism described above. The adjacent toothed paths may be formed by a single set of teeth and only notionally divided into separate paths based on the passage of the fingers along the rack.

The tactile/audible feedback may be generated by using enlarged teeth, as described, or may alternatively be generated by controlling the biasing force of the fingers.

The or each actuation button may carry a plurality of fingers which simultaneously engage with the teeth to provide improved engagement.

Although the pawl element 28 been described as using a torsion bar design, it will be appreciated that other arrangements may be used, such as a cantilever design. In certain applications, the pawl element 28 may also be integrally formed with the first arcuate member 4a.

Figure 8:
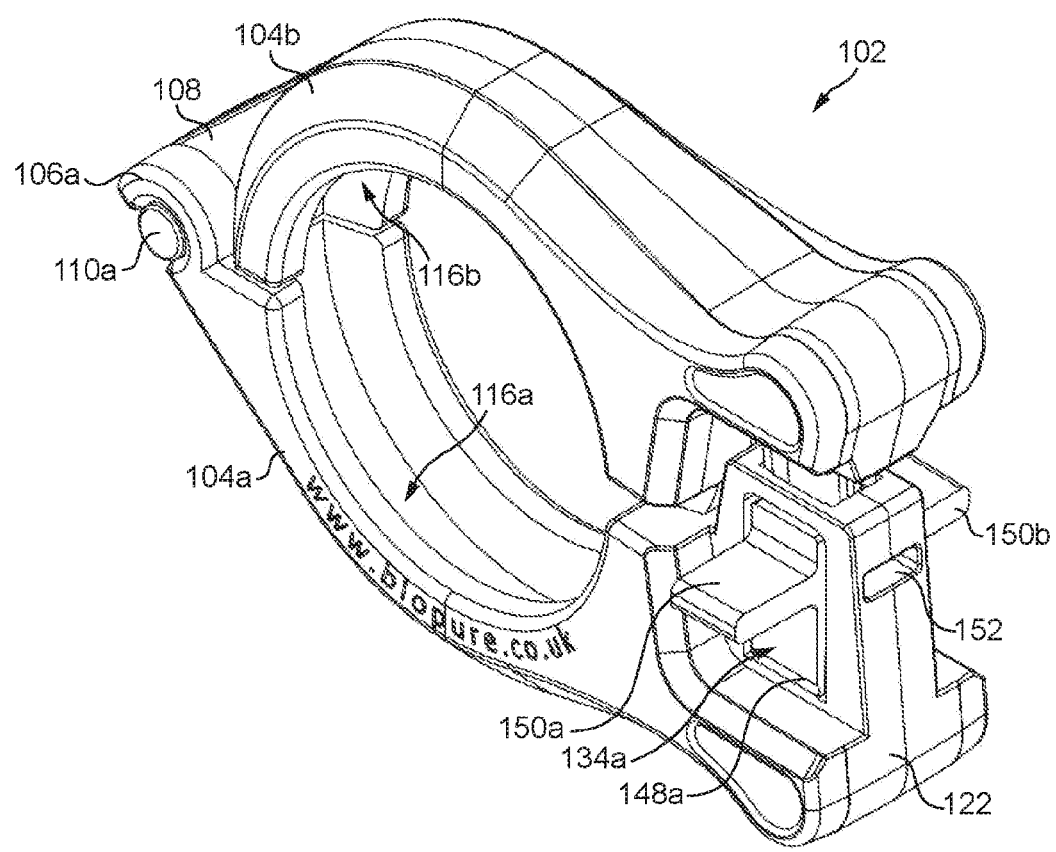
FIG. 8 is a perspective view of a clamp according to another embodiment of the invention in a closed position.
Figure 9:
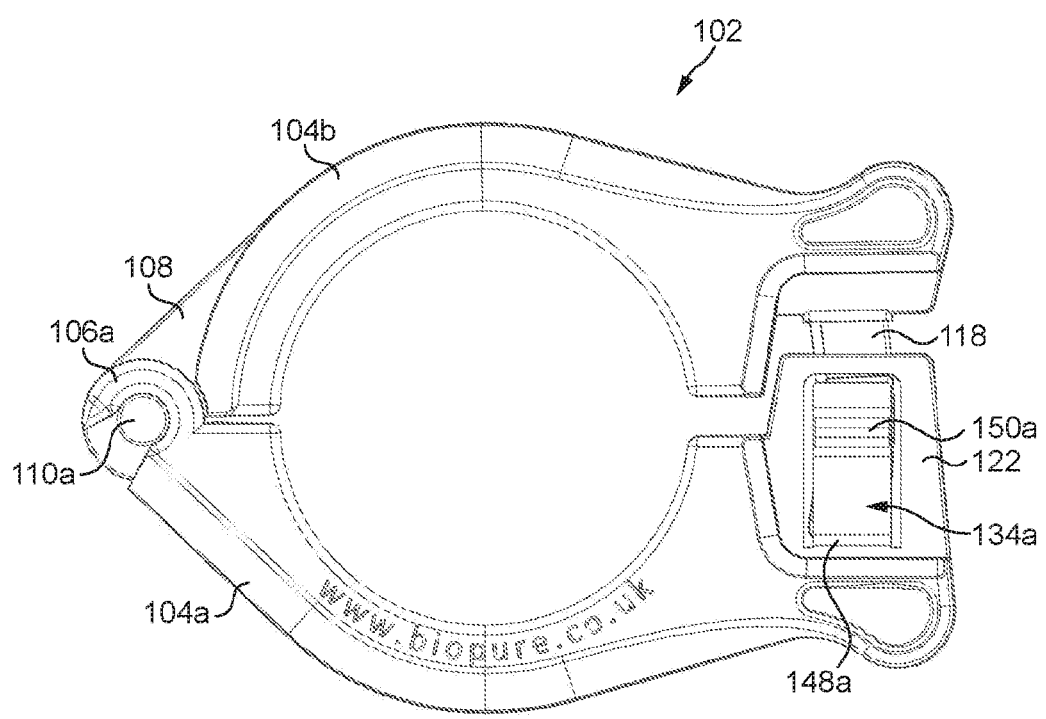
FIG. 9 is a side view of the clamp of FIG. 8.
Figure 10:
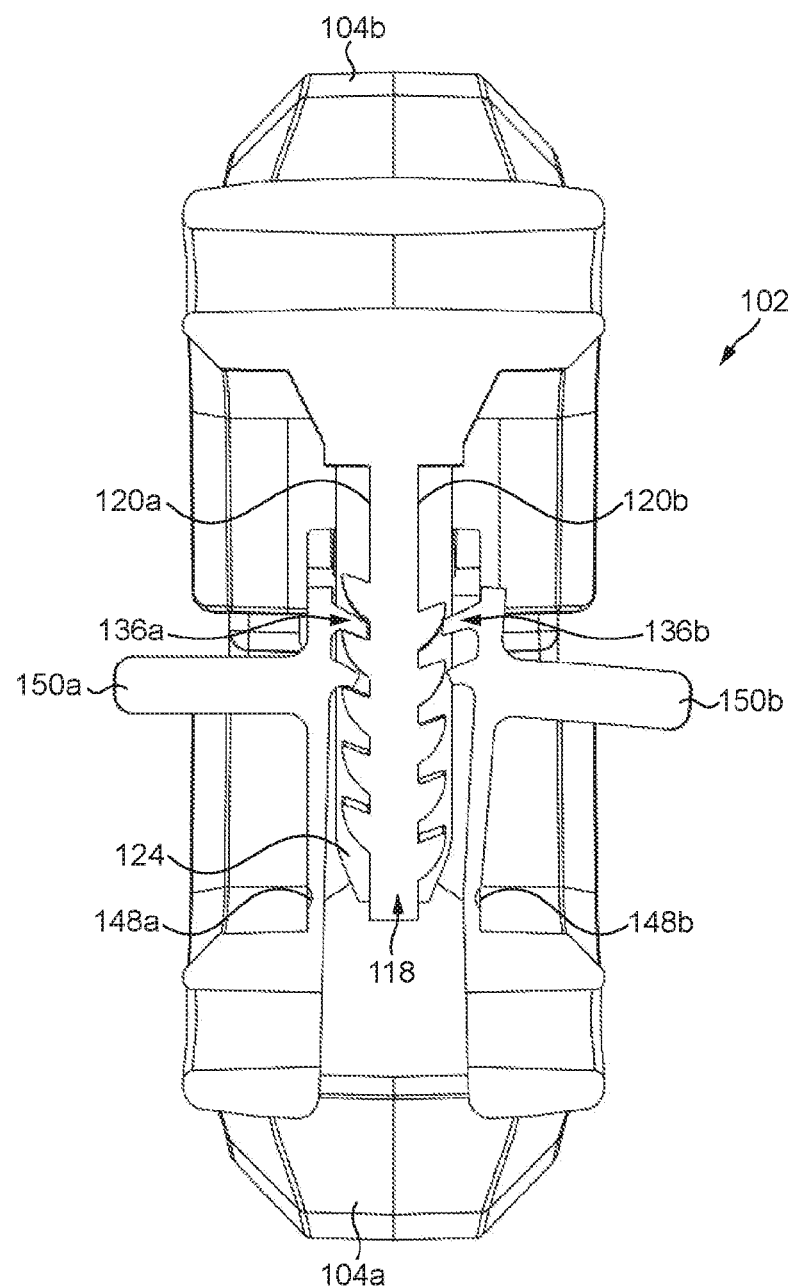
FIG. 10 is a cross-sectional view showing a ratchet mechanism of the clamp of FIG. 8.

FIGS. 8 to 10 show a clamp 102 according to another embodiment of the invention. The clamp 102 is similar to the clamp 2 described previously in many respects, but differs primarily in that it does not include a separate pawl element which is detachably connected to the clamp.

The clamp 102 again comprises a first, lower arcuate portion 104a and a second, upper arcuate portion 104b which are hingedly connected to one another in a similar manner to that described for the clamp 2.

As described for the clamp 2, the clamp 102 comprises a ratchet mechanism for locking the clamp 102 in the closed position. Specifically, the second arcuate portion 104b is provided with a tongue 118 (rack) which comprises opposing lateral surfaces 120a, 120b which are each provided with one or more teeth. The first arcuate portion 104a is provided with a receiving portion 122. The receiving portion 122 defines a cavity 124 (see FIG. 10) which receives the tongue 118. Each lateral side of the receiving portion 122 comprises a pawl portion 134a, 134b. The pawl portions 134a, 134b are connected to the receiving portion 122 only at their lower ends. The pawl portions 134a, 134b are therefore cantilevered and are allowed to pivot about their lower ends via a thinned section 148a, 148b which forms a hinge (see FIG. 10). A release tab 150a, 150b protrudes perpendicularly from each pawl portion 134a, 134b. The release tabs 150a, 150b are positioned towards the free end of the pawl portions 134a, 134b and thus are spaced from the hinged ends.

As shown in FIG. 10, each of the pawl portions 134a, 134b is provided with a pair of fingers 136a, 136b (only one finger may be used in other embodiments) which are spaced from the hinged ends of the pawl portion 134a, 134b. The fingers 136a, 136b are configured to engage with the teeth of the opposing lateral surfaces 120a, 120b of the tongue 118 respectively.

The free ends of the pawl portions 134a, 134b are biased towards one another so that the fingers 136a, 136b engage with the teeth of the opposing lateral surfaces 120a, 120b of the tongue 118. The fingers 136a, 136b may be drawn away from the tongue 18 by pivoting the pawl portions 134a, 134b about the hinged ends. The clamp 102 may be held such that the operators thumb is positioned under the lower arcuate portion 104a, and the index and middle finger are on top of the release tabs 150a, 150b. The release tabs 150a, 150b may be pulled down so that they pivot about the hinged ends, thereby drawing the fingers 136a, 136b away from one another and out of engagement with the teeth of the tongue 118 so that the clamp 102 can be opened. The pawl portions 134a, 134b are resilient such that the fingers 136a, 136b are forced back towards one another once the release tabs 150a, 150b are released.

As shown in FIG. 8, the receiving portion 122 may be provided with an aperture 152 formed in its radial, end surface which allows the radial, end surface of the tongue 118 to be viewed when it is received within the receiving portion 122. The radial, end surface of the tongue 118 may comprise a graduated scale along its length which is visible through the aperture 152 and thus provides an indication of the position of the tongue 118 within the receiving portion 122 and thus the relative positions of the arcuate portions 104a, 104b. The scale can therefore be used to ensure that the clamp 102 has been closed sufficiently.

Figure 11:
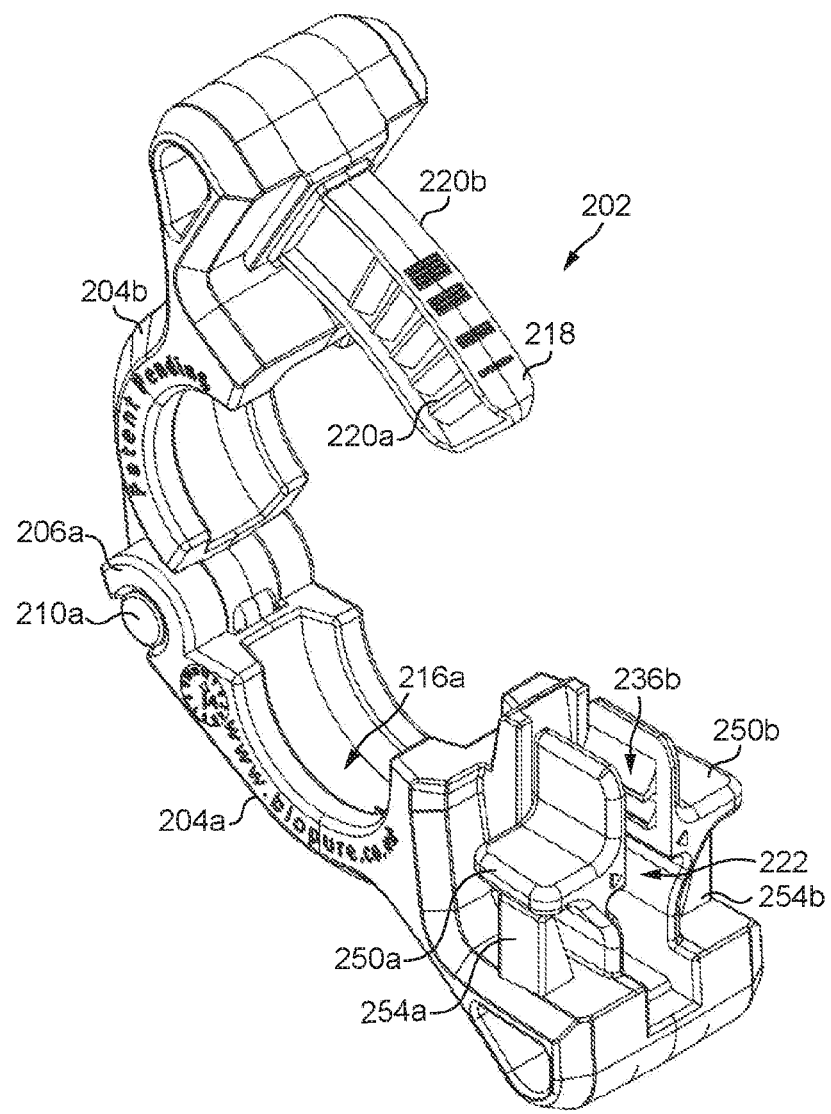
FIG. 11 is a perspective view of a clamp according to another embodiment of the invention in an open position.
Figure 12:
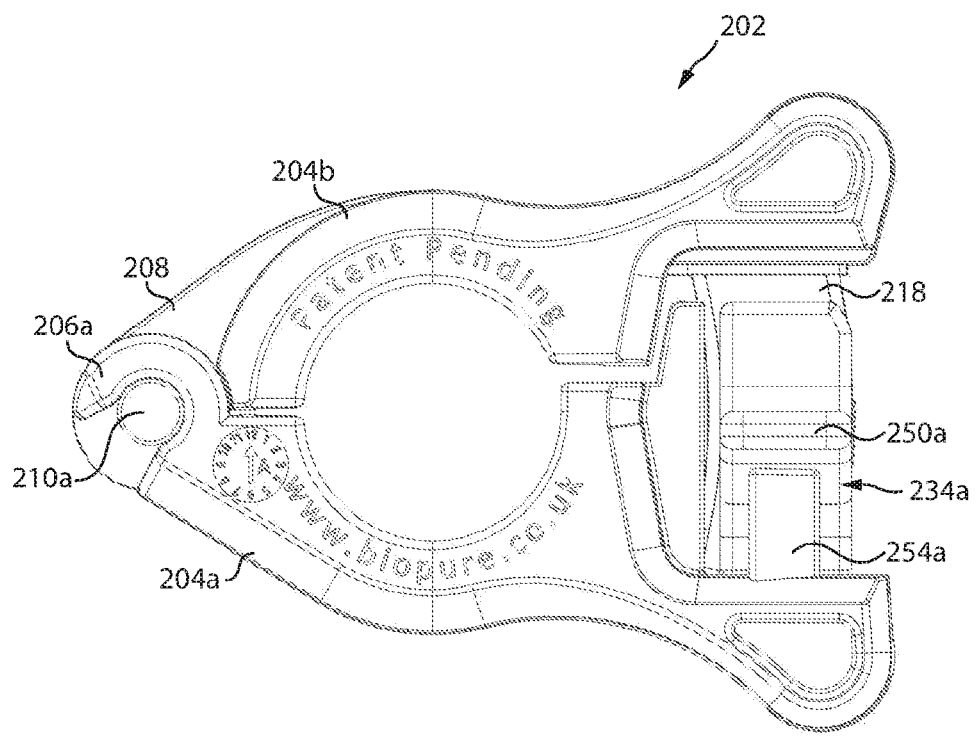
FIG. 12 is a side view of the clamp of FIG. 11 in a closed position.
Figure 13:
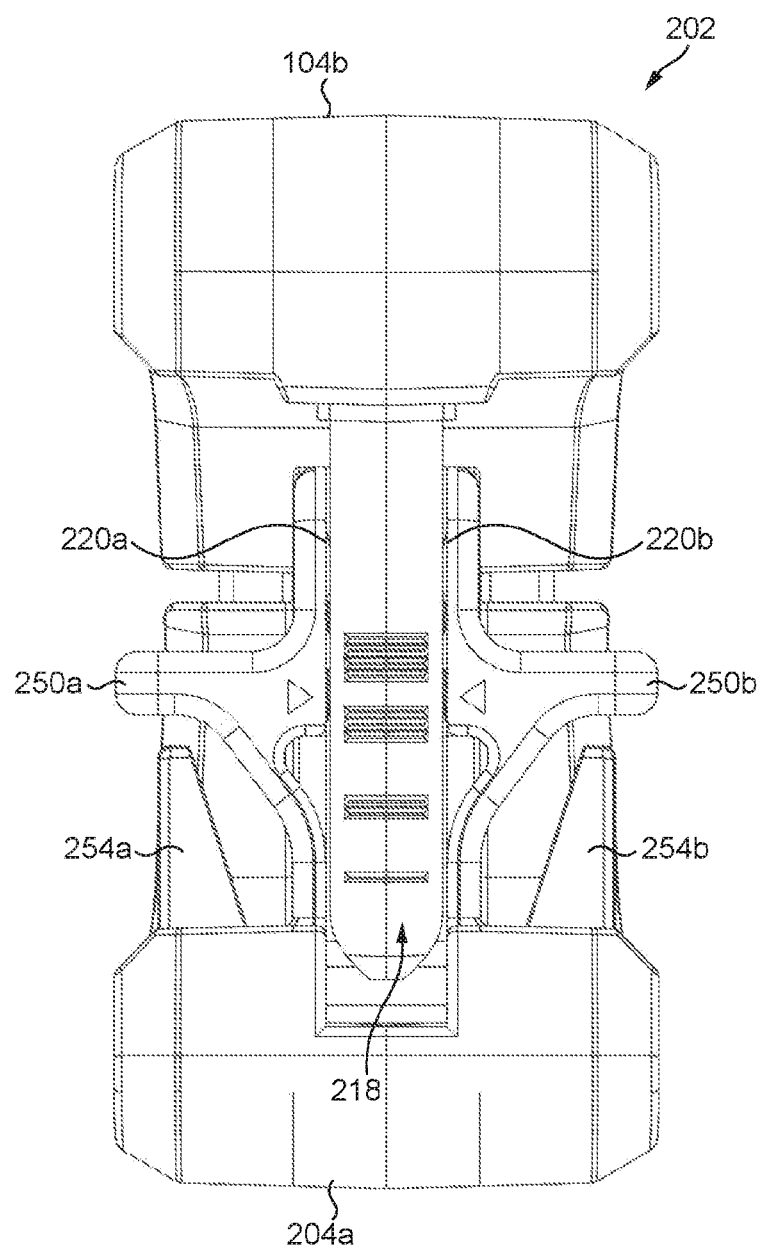
FIG. 13 is a front view showing a ratchet mechanism of the clamp of FIG. 11.
Figure 14:
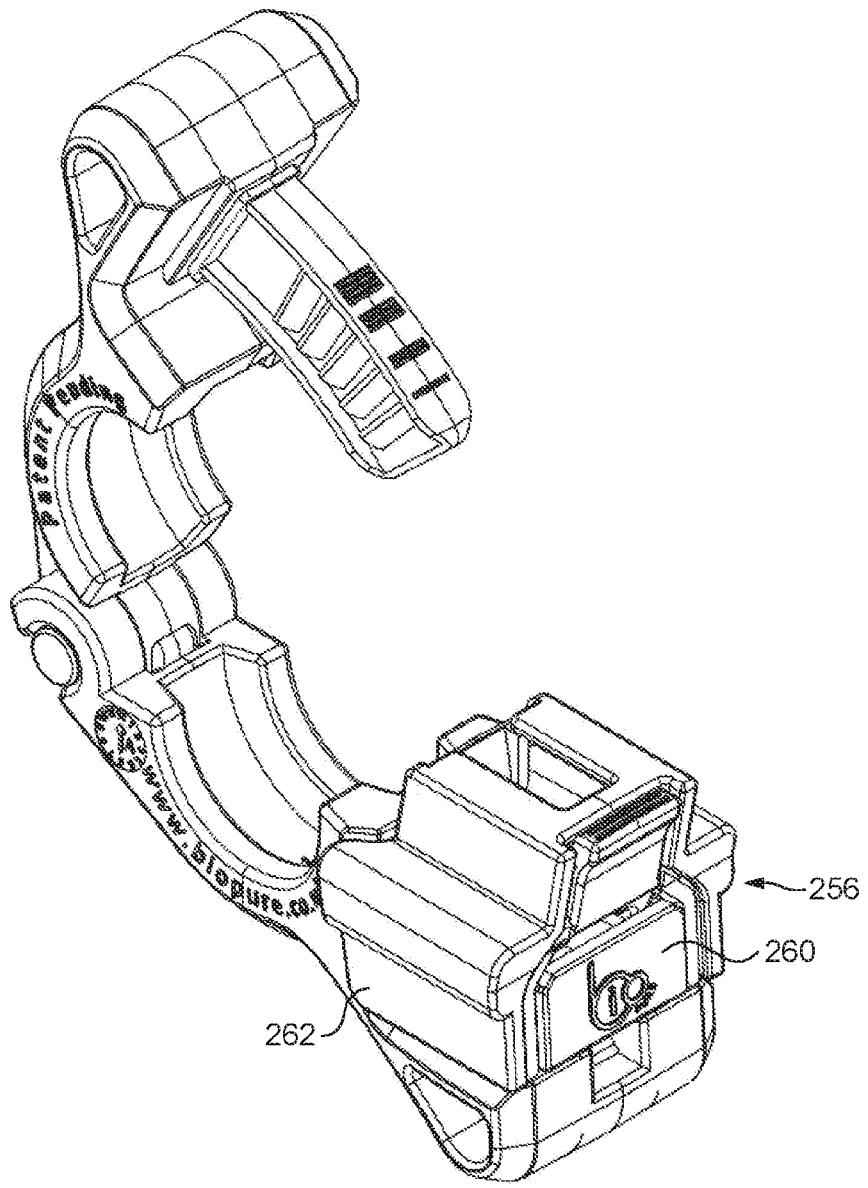
FIG. 14 is a perspective view of the clamp of FIG. 11 with a tamper-evident cover fitted thereto.
Figure 15:
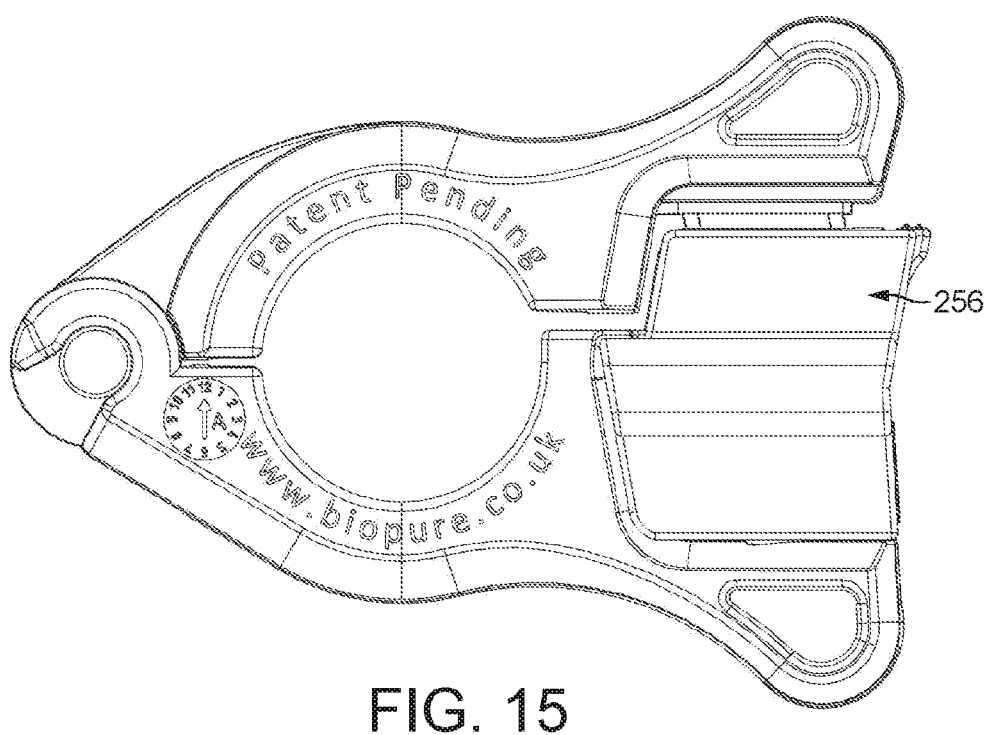
FIG. 15 is a side view of the clamp and tamper-evident cover shown in FIG. 14.
Figure 16:
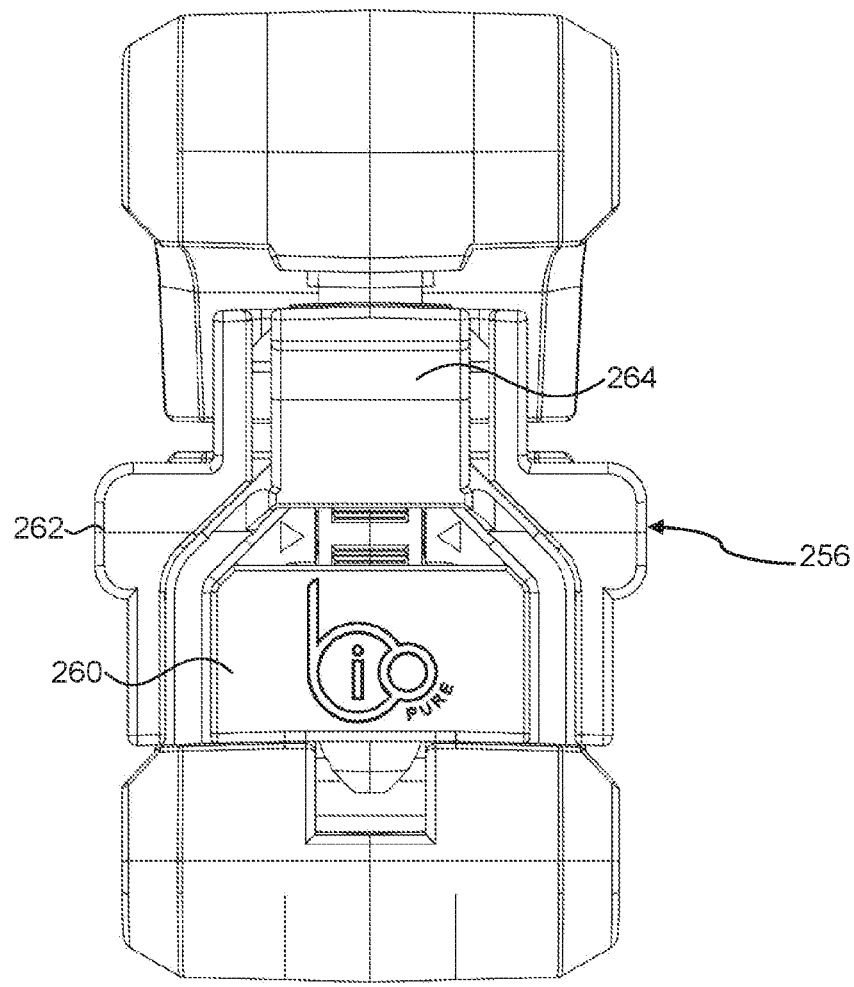
FIG. 16 a front view of the clamp and tamper-evident cover shown in FIG. 14.

FIGS. 11 to 13 show a clamp 202 according to another embodiment of the invention. The clamp 202 is similar to the clamp 102 described previously in many respects, but the structure of the receiving portion 222 differs from that described previously.

The clamp 202 again comprises a first, lower arcuate portion 204a and a second, upper arcuate portion 204b which are hingedly connected to one another in a similar manner to that described for the previous clamps 2, 102. The first and second arcuate portions 204a, 204b differ slightly from those described previously in that the first, lower arcuate portion 204a extends around more than 180 degrees of the hose tail fittings. In other words, the first and second arcuate portions 204a, 204b are not equal halves, with the first arcuate portion 204a extending over 192 degrees. This helps retain the components prior to clamping.

As described for the clamps 2, 102, the clamp 202 comprises a ratchet mechanism for locking the clamp 202 in the closed position. Specifically, the second arcuate portion 204b is provided with a tongue 218 (rack) which comprises opposing lateral surfaces 220a, 220b which are each provided with one or more teeth. The first arcuate portion 204a is provided with a receiving portion 222. The receiving portion 222 is defined by pawl portions 234a, 234b at either lateral side of the clamp 202. The pawl portions 234a, 234b are connected only at their lower ends. The pawl portions 234a, 234b are therefore cantilevered and are allowed to pivot about their lower ends. A release tab 250a, 250b protrudes perpendicularly from each pawl portion 234a, 234b.

Each of the pawl portions 234a, 234b is provided with a pair of fingers 236a, 236b (only the pair of fingers 236b is visible in FIG. 11; only one finger may be used in other embodiments) which are spaced from the hinged ends of the pawl portion 234a, 234b. The fingers 236a, 236b are configured to engage with the teeth of the opposing lateral surfaces 220a, 220b of the tongue 218 respectively.

Each pair of fingers 236a, 236b forms a primary, upper finger and a secondary, lower finger. The primary finger may be larger than the secondary finger. The primary finger may be used predominantly when the clamp is closed. The secondary finger engages with the tongue 218 and is used to increase the contact area when the clamp is under pressure. This effectively spreads the load between the two fingers, and acts as a backup in the unlikely event that the primary finger slips. A rib may be provided between the fingers at the innermost edge so as to join the fingers together. This rib reinforces both fingers and prevents deformation during pressurization following an autoclaving procedure. A corresponding slot may be provided in the tongue 218 to receive the rib between the fingers 236a, 236b.

The pawl portions 234a, 234b are cranked so that when vertical force is applied to the release tabs 250a, 250b, the pawl portions 234a, 234b move away from the tongue 218. This reduces the forces required to open the clamp.

A pair of tab stops 254a, 254b are provided to limit movement of the pawl portions 234a, 234b. The tab stops 254a, 254b are disposed beneath the release tabs 250a, 250b respectively and contact the release tabs 250a, 250b when they are pulled down to open the clamp 202. The tab stops 254a, 254b therefore prevent the pawl portions 234a, 234b from being opened excessively which could otherwise cause them to be permanently deformed. The tab stops 254a, 254b also serve a secondary purpose in that they prevent the user from placing their fingers under the release tabs 250a, 250b and thus convey to the user the correct way of opening the clamp.

As shown in FIG. 13, the radial, end surface of the tongue 218 may comprise a graduated scale or other indicia along its length which is visible between the pawl portions 234a, 234b and thus provides an indication of the position of the tongue 218 within the receiving portion 222 and thus the relative positions of the arcuate portions 204a, 204b. The scale can therefore be used to ensure that the clamp 202 has been closed sufficiently. The pawl portions 234a, 234b may be provided with reference indicia such as arrows which are used to define the relative position of the scale on the tongue 218.

FIGS. 14 to 17 show a tamper-evident cover 256 which is snap-fitted onto the clamp and is used to conceal the pawl portions 234a, 234b to prevent them from being actuated and the clamp 202 opened.

The cover 256 is a plastic injection molded product made from polypropylene. The cover 256 forms a cavity which has a cross-section that approximately conforms to the outer profile of the receiving portion 222 (i.e. the pawl portions 234a, 234b and the tab stops 254a, 254b). The cover 256 can therefore be introduced over the receiving portion 222 by sliding it in a radially inward direction over the pawl portions 234a, 234b and the tab stops 254a, 254b. The cover 256 is provided with internal ribs 257 which locate in the space provided between the tab stops 254a, 254b and the release tabs 250a, 250b. This ensures that the cover 256 does not rotate or twist during fitment.

Figure 17:
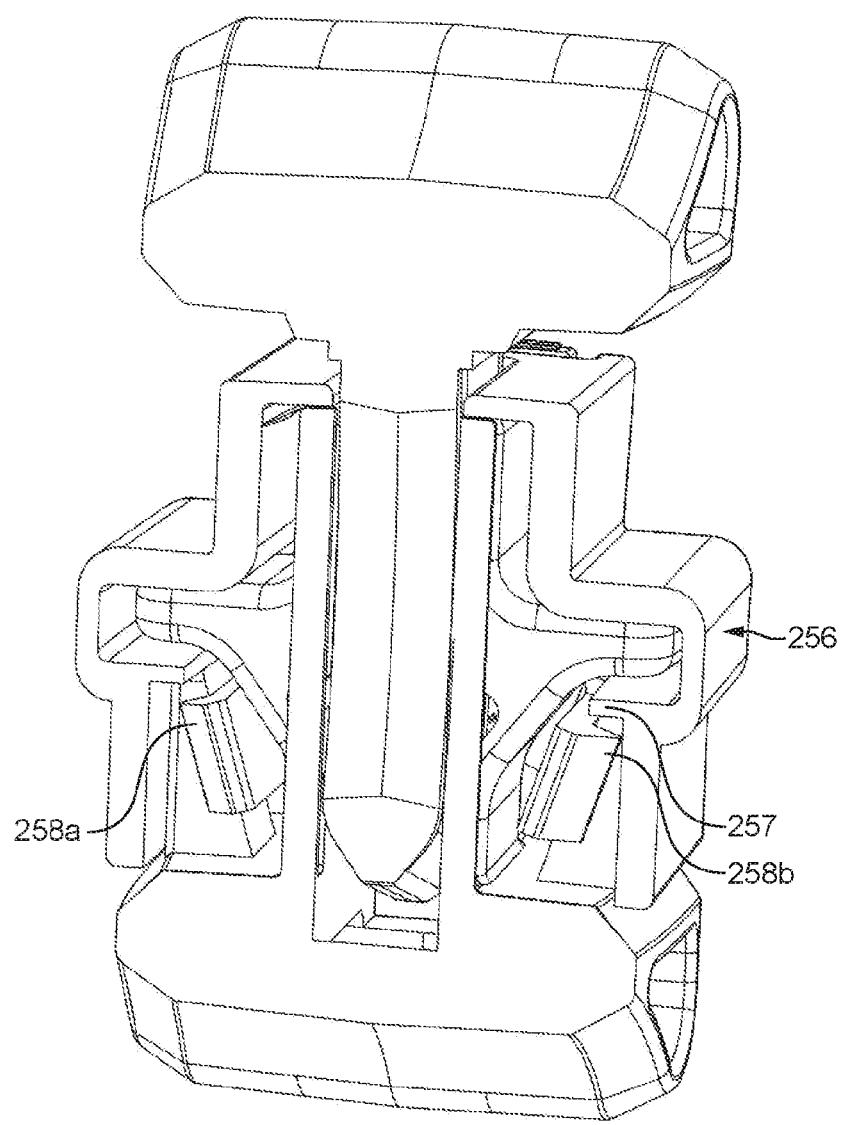
FIG. 17 is a cross-sectional view showing how the tamper-evident cover is affixed to the clamp.

As shown in FIG. 17, the cover 256 comprises a pair of barbs 258a, 258b which project within the cavity formed by the cover 256. As shown, the barbs 258a, 258b are configured to deflect inwards and pass between the tab stops 254a, 254b and the pawl portions 234a, 234b and for a head of each barb 258a, 258b to hook onto the backside of the tab stop 254a, 254b once it clears the tab stop 254a, 254b. The barbs 258a, 258b thus retain the cover 256 to prevent it being withdrawn from the receiving portion 222. Further, the barbs 258, 258b are concealed within the cover 256 such that they cannot be accessed once the cover 256 has been fitted.

The cover 256 forms a slot for receiving the tongue 218 such that it can pass between and engage with the pawl portions 234a, 234b. The cross-section of the cover 256 may be such that some movement of the release tabs 250a, 250b is permitted so that the tongue 218 can be inserted between the pawl portions 234a, 234b with the cover in-situ. However, once the clamp 202 has been closed with the tongue 218 inserted into the receiving portion 222, then it cannot be opened since the cover 256 prevents access to the release tabs 250a, 250b. Further, the cover 256 is made of sufficiently strong material that it cannot be deformed to allow the release tabs 250a, 250b to be actuated externally. The clamp 202 can only be opened by removing the cover 256. The removal of the cover 256 is immediately evident and so the cover 256 prevents someone from tampering with the clamp 202.

Figure 18:
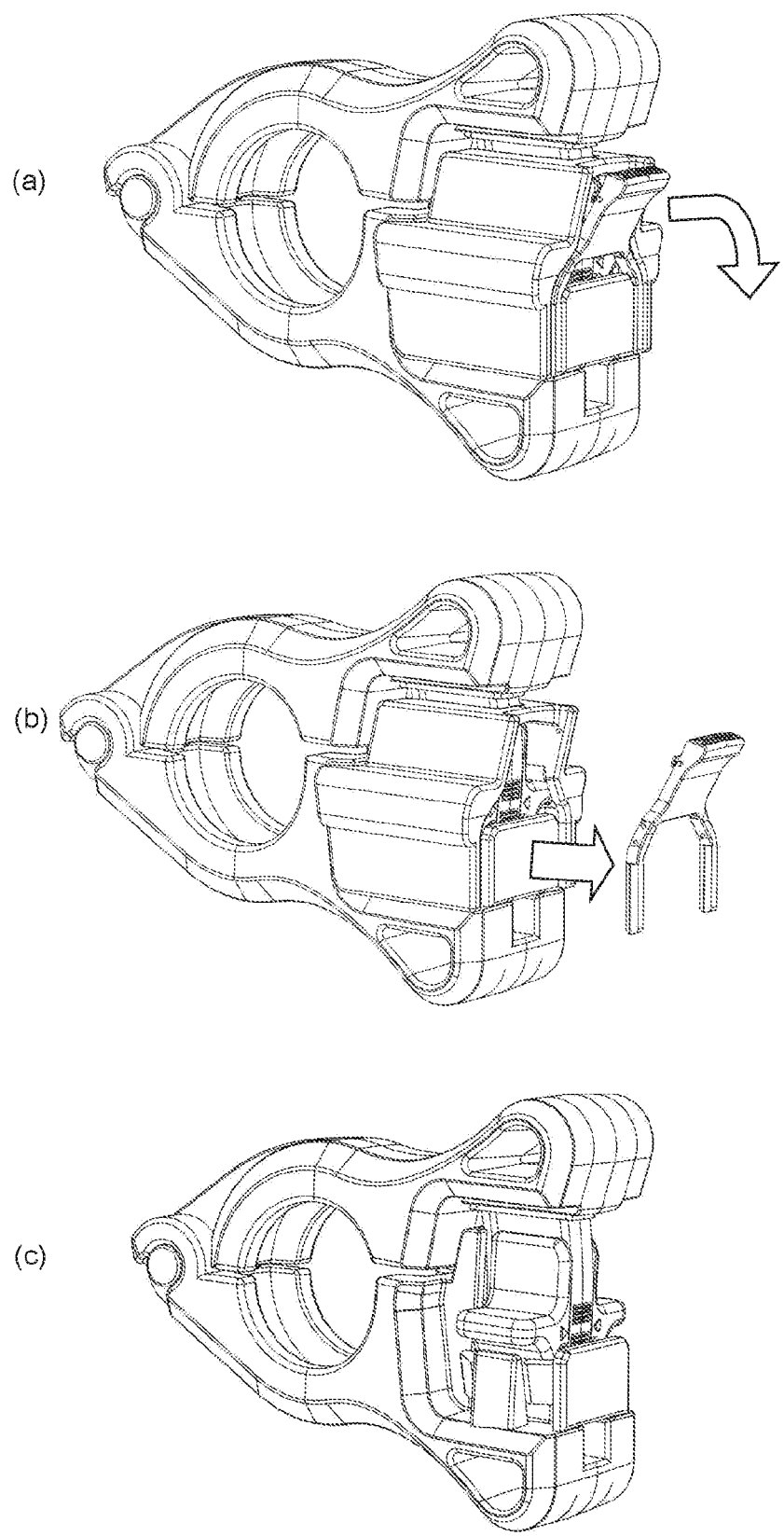
FIG. 18 illustrates how the tamper-evident cover is removed from the clamp.

The cover 256 is formed by a first, insert portion 260 and a second, peripheral portion 262 which are connected to one another by a pull-tab 264. The insert portion 260 carries the barbs 258a, 258b, whereas the peripheral portion 262 defines the outer periphery (i.e. the cross section) of the cover 256. An opening is formed between the pull-tab 264 and the insert portion 260 through which the indicia provided on the radial, end surface of the tongue 218 can be seen. The pull-tab 264 comprises a tab portion and a pair of tail portions extending from the tab portion. The tab portion is connected to the peripheral portion 262 by a frangible pip. The tail portions of the pull-tab 264 are each connected to the insert portion 260 and the peripheral portion 262 via thinned webs or membranes which form tear lines and allow the tail portions and thus the pull-tab 264 to be easily pulled away from the insert portion 260 and the peripheral portion 262 via the tab portion by tearing through the webs. The removal of the pull-tab 264 thus separates the insert portion 260 from the peripheral portion 262. Consequently, the peripheral portion 262 is no longer constrained by the barbs 258a, 258b and so can be removed from the clamp 202. This allows the release tabs 250a, 250b to be accessed and actuated so that the clamp 202 can be opened. The insert portion 260 can also be removed from the clamp 202 by forcing the barbs 258a, 258b over the tab stops 254a, 254b. This process is shown in FIG. 18.

It will be appreciated that the structure of the tamper-evident cover could be adapted to also engage with the clamps 2, 102 in a similar manner.

Although the tamper-evident cover has been described with reference to a clamp, it will be appreciated that it may be used with other components. In particular, the tamper-evident cover may be used to conceal an actuator mechanism of a component in order to prevent it from being accessed and unwantedly activated. For example, the tamper-evident cover may be used with a flow control and/or shut off valve (such as the BioPure BioValve™) in order to prevent access to a handle or other actuator which may be used to open or close the valve.

To avoid unnecessary duplication of effort and repetition of text in the specification, certain features are described in relation to only one or several aspects or embodiments of the invention. However, it is to be understood that, where it is technically possible, features described in relation to any aspect or embodiment of the invention may also be used with any other aspect or embodiment of the invention.

It will be appreciated that the first and second arcuate portions need not be semi-circular and that additional (arcuate or non-arcuate) portions may be disposed between the first and second arcuate portions. The second arcuate portion may therefore be hingedly connected to the first arcuate portion via one or more additional portions.

The invention is not limited to the embodiments described herein, and may be modified or adapted without departing from the scope of the present invention.

The invention claimed is:

1. A tamper-evident cover for a component, the component including a first portion and a second portion, and an actuator mechanism for moving the first and second portions or allowing the first and second portions to move relative to one another, the tamper-evident cover comprising:
   a cover portion defining a cavity configured to receive the actuator mechanism of the component to prevent access to the actuator mechanism from the exterior of the cover portion;
   a retention barb connected to the cover portion and housed within the cavity formed by the cover portion such that it is inaccessible from the exterior of the cover portion, the retention barb being configured to engage with the component so as to retain the cover portion over the actuator mechanism; and
   wherein the component is a clamp, wherein the first and second portions are arcuate portions which are hingedly connected to one another and the actuator mechanism is a ratchet mechanism for locking the first and second arcuate portions in a closed position, the ratchet mechanism comprising a toothed rack provided with the second arcuate portion and a pawl provided with the first arcuate portion for engaging with the rack;
   wherein the cavity of the cover portion is configured to receive the ratchet mechanism of the clamp so as to prevent access to the pawl from the exterior of the cover portion; and
   wherein the pawl of the clamp comprises a release tab and a tab stop, and wherein the retention barb is configured to pass between the release tab and the tab stop and engage with the tab stop.

2. A tamper-evident cover for a component, the component including a first portion and a second portion, and an actuator mechanism for moving the first and second portions or allowing the first and second portions to move relative to one another, the tamper-evident cover comprising:
   a cover portion defining a cavity configured to receive the actuator mechanism of the component to prevent access to the actuator mechanism from the exterior of the cover portion;
   a retention barb connected to the cover portion and housed within the cavity formed by the cover portion such that it is inaccessible from the exterior of the cover portion, the retention barb being configured to engage with the component so as to retain the cover portion over the actuator mechanism;
   wherein the cover portion is formed by a first element and the retention barb is formed by a second element, wherein the first and second elements are separable from one another such that the cover portion can be removed to provide access to the actuator mechanism; and
   wherein the first and second elements are connected by a pull-tab which is removable to separate the first and second elements.

* * * * *